(12) United States Patent
Bachmaier (10) Patent No.: US 9,603,712 B2
(45) Date of Patent: Mar. 28, 2017

(54) SHOULDER IMPLANT WITH STEM

(71) Applicant: Arthrex, Inc., Naples, FL (US)

(72) Inventor: Samuel Bachmaier, Mauern (DE)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 14/540,120

(22) Filed: Nov. 13, 2014

(65) Prior Publication Data

US 2015/0134066 A1    May 14, 2015

(30) Foreign Application Priority Data

Nov. 14, 2013  (EP) .................................... 13192983

(51) Int. Cl.
*A61F 2/40* (2006.01)
*A61F 2/30* (2006.01)

(52) U.S. Cl.
CPC .......... *A61F 2/4014* (2013.01); *A61F 2/4059* (2013.01); *A61F 2002/3038* (2013.01); *A61F 2002/30604* (2013.01); *A61F 2002/4018* (2013.01); *A61F 2002/4022* (2013.01); *A61F 2002/4037* (2013.01); *A61F 2002/4051* (2013.01); *A61F 2002/4074* (2013.01); *A61F 2220/0025* (2013.01)

(58) Field of Classification Search
CPC ........ A61F 2/38; A61F 2/3804; A61F 2/3854; A61F 2/3859; A61F 2/40; A61F 2/4059; A61F 2/4081; A61F 2/42; A61F 2/4261; A61F 2002/3809; A61F 2002/3813; A61F 2002/3822; A61F 2002/4022; A61F 2/4014; A61F 2/4003

USPC ........................ 623/19.11–19.14, 22.4, 22.42
See application file for complete search history.

(56) References Cited

U.S. PATENT DOCUMENTS

| | | | | |
|---|---|---|---|---|
| 5,507,819 | A * | 4/1996 | Wolf | A61F 2/4081 623/19.11 |
| 5,702,457 | A * | 12/1997 | Walch | A61F 2/4014 623/19.13 |
| 6,790,234 | B1 * | 9/2004 | Frankle | A61F 2/40 623/19.12 |
| 6,899,736 | B1 * | 5/2005 | Rauscher | A61F 2/40 623/19.12 |
| 7,445,638 | B2 | 11/2008 | Beguin et al. | |
| 7,819,923 | B2 | 10/2010 | Stone et al. | |
| 8,118,875 | B2 * | 2/2012 | Rollet | A61F 2/4014 623/18.11 |
| 8,512,410 | B2 * | 8/2013 | Metcalfe | A61F 2/4003 623/19.14 |
| 8,608,805 | B2 * | 12/2013 | Forrer | 623/19.12 |
| 8,623,092 | B2 * | 1/2014 | Bickley | A61F 2/40 623/18.11 |

(Continued)

*Primary Examiner* — Alvin Stewart
(74) *Attorney, Agent, or Firm* — Karish & Bjorgum, PC (57) ABSTRACT

A humerus implant has a stem, cup shaped body and a locking adapter. The cup shaped body is locked to the stem by a key-slot mechanism. The cup shaped body has a center portion and a plurality of flexible first sidewall segments and second sidewall segments, with gaps between neighbored sidewall segments. The first sidewall segments have a plurality of locking fins while the second sidewall segments having a plurality of recesses and holes. The locking adapter has means for fixing the locking adapter to the cup shaped body and a locking ring for locking the sidewall segments into their final positions.

19 Claims, 10 Drawing Sheets

(56) References Cited

U.S. PATENT DOCUMENTS

| Patent/Pub. No. | Date | Inventor | Class |
|---|---|---|---|
| 8,936,645 B1* | 1/2015 | Masson | A61F 2/30728 623/19.11 |
| 8,945,234 B2* | 2/2015 | Humphrey | A61F 2/30 623/19.14 |
| 2004/0220673 A1* | 11/2004 | Pria | A61F 2/4081 623/19.12 |
| 2005/0278031 A1* | 12/2005 | Tornier | A61F 2/40 623/19.12 |
| 2006/0069443 A1* | 3/2006 | Deffenbaugh | A61F 2/4081 623/19.11 |
| 2006/0200249 A1* | 9/2006 | Beguin | A61F 2/4014 623/19.14 |
| 2007/0156246 A1* | 7/2007 | Meswania | A61F 2/40 623/19.12 |
| 2007/0173945 A1* | 7/2007 | Wiley | A61F 2/30734 623/19.13 |
| 2008/0183297 A1* | 7/2008 | Boileau | A61F 2/4081 623/19.14 |
| 2009/0076621 A1 | 3/2009 | Rollet | |
| 2009/0099662 A1* | 4/2009 | Splieth | A61F 2/4684 623/19.14 |
| 2009/0112328 A1* | 4/2009 | Tornier | A61F 2/40 623/18.11 |
| 2009/0149961 A1* | 6/2009 | Dallmann | A61F 2/4003 623/19.11 |
| 2009/0164021 A1* | 6/2009 | Dallmann | A61F 2/40 623/19.11 |
| 2009/0171462 A1* | 7/2009 | Poncet | A61F 2/4014 623/19.12 |
| 2009/0210065 A1* | 8/2009 | Nerot | A61F 2/4014 623/19.14 |
| 2009/0281630 A1* | 11/2009 | Delince | A61F 2/4081 623/19.13 |
| 2009/0306782 A1* | 12/2009 | Schwyzer | A61F 2/4003 623/19.12 |
| 2010/0211178 A1* | 8/2010 | Nogarin | A61F 2/40 623/19.14 |
| 2010/0234959 A1* | 9/2010 | Roche | A61F 2/40 623/19.13 |
| 2011/0060417 A1* | 3/2011 | Simmen | A61F 2/4014 623/19.11 |
| 2012/0179262 A1* | 7/2012 | Metcalfe | A61F 2/4014 623/19.14 |
| 2012/0179263 A1* | 7/2012 | Metcalfe | A61F 2/40 623/19.14 |
| 2012/0253467 A1* | 10/2012 | Frankle | A61F 2/40 623/19.11 |
| 2012/0271425 A1* | 10/2012 | Maurer | A61F 2/32 623/19.12 |
| 2012/0303130 A1* | 11/2012 | Winslow | A61F 2/4081 623/19.12 |
| 2013/0053969 A1* | 2/2013 | Linares | A61F 2/40 623/19.13 |
| 2013/0066433 A1* | 3/2013 | Veronesi | A61F 2/4081 623/19.13 |
| 2013/0090736 A1* | 4/2013 | Katrana | A61F 2/4014 623/19.13 |
| 2013/0204375 A1* | 8/2013 | Winslow | A61F 2/40 623/19.13 |
| 2013/0245775 A1* | 9/2013 | Metcalfe | A61F 2/40 623/19.12 |
| 2013/0261750 A1* | 10/2013 | Lappin | A61F 2/4081 623/19.11 |
| 2013/0261751 A1* | 10/2013 | Lappin | A61F 2/4081 623/19.11 |
| 2013/0261752 A1* | 10/2013 | Lappin | A61F 2/28 623/19.11 |
| 2013/0282129 A1* | 10/2013 | Phipps | A61F 2/4081 623/19.11 |
| 2013/0289738 A1* | 10/2013 | Humphrey | A61F 2/30 623/23.42 |
| 2013/0325131 A1* | 12/2013 | Roche | A61F 2/40 623/19.13 |
| 2013/0325133 A1* | 12/2013 | Viscardi | A61F 2/4003 623/19.14 |
| 2014/0128982 A1* | 5/2014 | Termanini | A61F 2/34 623/19.13 |
| 2014/0236304 A1* | 8/2014 | Hodorek | A61B 17/164 623/19.14 |
| 2014/0379089 A1* | 12/2014 | Bachmaier | A61F 2/4014 623/19.14 |
| 2015/0134066 A1* | 5/2015 | Bachmaier | A61F 2/4014 623/19.14 |
| 2015/0265411 A1* | 9/2015 | Deransart | A61F 2/4014 623/19.14 |

* cited by examiner

SHOULDER IMPLANT WITH STEM

PRIORITY CLAIM

This application claims priority to pending European Application No. 13192983.8 filed on Nov. 14, 2013.

BACKGROUND OF THE INVENTION

1. Field of the Invention

The present invention relates to a shoulder arthroplasty system to surgical reconstitution of the human or animal shoulder and, in particular, to a humerus implant.

2. Description of Relevant Art

The shoulder joint is a ball-and-socket joint, which has an exceptional range of motion. Shoulder instability and other maladies of the shoulder joint, such as arthrosis, may require a replacement of the joint.

A shoulder joint prosthesis, which includes the replacement of the convex head of the humerus, is disclosed in U.S. Pat. No. 7,819,923. It reflects the orientation and the center of rotation of actual joints. In the case of a worn or damaged rotator cuff or too much bone loss, such prosthesis would not recover the range of motion. In such a case, a reverse shoulder prosthesis may be preferable. An example of such prosthesis is disclosed in the U.S. Patent Application Publication No. 2009/0210065 A1. In such prosthesis, the humeral component includes a stem and a cup attached to the stem. The glenoid component supports a convex head, which articulates with the cup of the humeral component.

U.S. Pat. No. 7,445,638 B2 discloses an implant with the stem and a removable basket shaped support. This support is seated in the cavity of a humerus head and fixedly connected to the stem. A load bearing polyethylene insert is connected to a stem by a cylindrical shaft, which was inserted into a hole of the shaft, further fixing the removable basket shaped support to the stem.

An implant as disclosed in the US Patent Application Publication No. 2009/0306782 A1 requires only a minimum of bone material to be removed. Here fixation of the implant within the bone is far less stable compared to a stem.

An improved stemless implant is disclosed in the US Patent Application Publication No. 2012/0179263 A1 by the same inventors of this application. The implant has a cup shaped body with an outer thread. The thread has a plurality of fins with cutouts between the fins. The fins have inclined leading surfaces to minimize insertion torque.

SUMMARY OF THE INVENTION

The embodiments are based on the object of providing a humerus implant which may be used as part of a shoulder prosthesis and which can be securely fixed within the humerus with minimal removal of bone material. The fixation procedure should be simple and quick, requiring a low number of parts, increasing the efficiency of treatment and the risk associated therewith. A good fixation shall be achieved immediately after insertion, if required without cementing, so that the joint can be used immediately after insertion. A high retention force should be achieved. A precise placement and orientation of the implant should be possible. The Implant should be adaptable to different bone geometries.

In an embodiment, the implant comprises a cup shaped body having means for fixing the body within a cavity of the humerus head. The implant further comprises a stem to which the cup shaped body can directly be fixed. This embodiment allows for a significantly improved fixation of the implant within the humerus. Due to the direct connection of the cup shaped body to the stem, the implant is a rigid unit after assembly. The stem is anchored in the humerus and the cup shaped body is anchored in a cavity of the humerus head. This double anchoring results in a significantly improved stability. Preferably, the stem is cemented into a reamed hole of the humerus. The cup shaped body has means for fixing within a cavity of the humerus head.

In another embodiment, the humerus implant comprises a cup shaped body having flexible sidewall segments connected together at a center portion. There may be any number of sidewall segments between two and 24. Preferably, six sidewall segments are provided. There are at least two different types of sidewall segments. Whereas the sidewall segments basically have the same inner contour, they may differ in the outer shape, which has to provide a stable, secure and long-lasting contact with the surrounding bone. Preferably, four first sidewall segments and two second sidewall segments are provided. The different types of sidewall segments are optimized for different properties. A first type of sidewall segments preferably has a plurality of locking fins, which immediately anchor the cup shaped body within the bone. Due to the radial anchoring in the bone material, the fins cause a comparatively high pull out force of the implant. Further cementing is no more necessary. A second type of sidewall segments preferably has a structure of recesses and holes, which allow ingrowth of the bone. The recesses increase the pull out force of the cup shaped body, while the holes block rotation. Preferably, the at least two types of sidewall segments are at least partially arranged alternating. This allows for a good distribution of the properties of both kinds of sidewall segments over the circumference of the cup shaped body. To allow insertion of the cup shaped body into a bone, gaps are provided between the individual sidewall segments. Accordingly, the gaps are between neighbored segments. These allow a slight compression of the sidewall segments during insertion and therefore a reduction of the outer circumference of the cup shaped body. Due to be reduced circumference, the cup shaped body can easily be inserted into a hole of the bone.

It is further preferred, if there is at least one, preferably two tabs, close to the upper side of one or two sidewall segments and extending radially from the cup shaped body. The at least one tab preferably is essentially parallel to a plane defined by the upper ends of the sidewall segments. It allow for a precise alignment of the cup shaped body. First, the cup shaped body may be aligned, so that at least one tab is located on the bone surface. This allows an alignment of the tilt of the cup shaped body. With implants, known from prior art, a spherical implant can be inserted into a spherical hole under any tilt angle. This may lead to a misplacement of the implant. When the at least one tab contacts the bone surface, the implant is parallel to the bone surface, without any tilt error. Therefore, the insertion alignment is improved. The at least one tab further increases stability of the implant immediately after insertion. When the implant is correctly installed and the at least one tab contacts the bone surface, it can provide additional load bearing capacity and optional tilt moment and therefore increase the stability significantly.

Furthermore, the at least one tab allows orientation of the implant in rotation. The implant preferably has an outer structure of the sidewall segments, which is adapted to different bone structures to optimize the fixation within the bone. Therefore, the implant may not be rotational symmetrical. To prevent a wrong insertion of the implant, the at least one tab gives an indication of the correct rotation.

The stem has an anchoring section by which it is anchored in a hole of the humerus. Depending on the anchoring requirements, the anchoring section may be adapted in its length and/or diameter. For making a rigid connection to the cup shaped body, means for a key and slot connection are provided. Preferably, the key is at the stem, while the slot is in the cup shaped body. Most preferably, there is a plurality of keys, which may engage with the slot. The keys may be spaced apart in different distances to allow for assembly of the stem and the cup shaped body in different distances or different sizes. The key and slot connection allows for a quick and simple assembly of the implant resulting in a rigid and long-term stable unit.

Implanting the implant is a comparatively simple procedure. First, the stem is inserted into a hole of the humerus. Fixation may be improved by bone cement. Then, the cup shaped body is pushed into a cavity of the humerus head, engaging with the stem. In this step, the cup shaped body is a rotated, preferably about an angle of 90°, to allow the at least one key of the stem to be inserted into the slot of the cup shaped body. Insertion may further be simplified by compressing at least one, preferably a plurality and most preferably all of the sidewall segments to reduce the circumference of the cup shaped body. In the next step, the cup shaped body is rotated into its final angular position, causing the key of the stem to interface with the slot of the cup shaped body resulting in a fixed assembly of the stem and the cup shaped body. Now, the compressed sidewall segments may be released. In a final step, a locking adapter is inserted into the cup shaped body, spreading the sidewall segments to their final position and causing locking fins of the sidewalls segments to penetrate into the bone to look the cup shaped body within the cavity.

For simplified insertion, the locking adapter has a conical outer contour. It may also be a tapered shank. During insertion the sidewall segments slide at the conical outer contour and are continuously pressed outwards towards the bone. This presses the locking fins into the surrounding bone. It preferably provides a locking ring, which interfaces with the sidewall segments and locks the sidewall segments into their final position with respect to the bone. Preferably, the locking ring surrounds the edges of the sidewall segments to hold them firmly in their position independent of pushing or pulling forces. The locking adapter preferably has means for holding further components, like a spherical liner. Such means may be a rotational symmetric contour into which these further components may be snapped in. It is further preferred, if the locking adapter provides a hole for a screw corresponding to a thread in the cup shaped body. By means of these components, a screw may be used to hold the locking adapter at the cup shaped body. There may be further centering means for centering the locking adapter with in the cup shaped body. Preferably, the centering means has a cylindrical shape interfacing with a cylindrical part of the center portion of the cup shaped body.

In a further embodiment, there may be a second locking adapter, which has a tapered shank for holding a spherical cap, preferably for an anatomical application, which has a corresponding conical hole. There may be a simple press fit to hold these components together. There may be further snap-in the means. There may be variations of the cap deviating from a sphere and being adapted to specific anatomical requirements According to another embodiment, the humerus implant has a cup shaped body having sidewalls between a top side and a bottom side. At the outside of the body is a thread having a plurality of fins starting with a first fin and ending with a last fin. There are cutouts between the fins. The fins are specifically designed to secure the body within the bone even without cementing. Due to the radial anchoring in the bone material, the fins cause a comparatively high pull out force of the implant. At least one fin, preferably a plurality of fins, most preferably all fins have an inclined leading surface which helps in incising into the bone by rotating the body in an inward direction. By this measure, the insertion torque is minimized. The inclination of the leading surface may also be negative resulting in an undercut leading surface. There may be a combination of different types of fins in one thread. Furthermore at least one fin, preferably a plurality of fins, most preferably all fins have a forward oriented undercut trailing surface. This results in an angle of less than 90 degrees between a top surface and the trailing surface, blocking rotation in the opposite, outward direction. Therefore, the removal torque is maximized. Between the individual fins there are cutouts leaving room for abraded bone material and therefore further reducing the insertion torque and avoiding chattering. Tests have proven that this thread design results in removal torques similar to and preferably at least 60% of insertion torques immediately after insertion and without any recovery period allowing further bone growth into the structure. Due to such bone growth, the removal torque increases further with time.

It is further preferable, if the top surface is also slightly inclining. It is preferred to have approximately straight leading, top and trailing surfaces, although any one or multiple surfaces may be rounded or arc shaped, which may result in a sawtooth like design.

By filling the cutouts with cement or bone grafts or substitutes the stability may further be increased.

In a preferred embodiment at least one fin, preferably a plurality of fins, and most preferably all fins extend in a radial direction from the cup shaped body.

The humerus implant may directly interface with the glenoid component of a reverse (inverse) shoulder prosthesis. It may also be designed to hold a joint adapter to interface with the glenoid component of a reverse shoulder prosthesis. In this case, the joint adapter is inserted into the cup shaped body preferably by means of a second locking adapter. It may furthermore be designed to hold the humerus component of an anatomical prosthesis.

In another embodiment, the humerus implant is designed to provide an interface for the humeral component of an anatomical prosthesis.

In the most preferred embodiment, it is designed to provide a combination interface for a joint adapter to interface with the glenoid component of a reverse prosthesis and the humeral component of an anatomical prosthesis. Here specifically the cup shape allows a more simple and robust interface for the humeral component of an anatomical prosthesis, which for example may be held by a Morse taper. This embodiment allows simple replacement of an anatomical prosthesis by a reverse prosthesis during revision. Here exchanging of a prosthesis stem is no more necessary. Even the implant can remain in place, as only the heads must be exchanged.

The humerus implant may be manufactured from Titanium alloy, or other biocompatible metallic or non-metallic materials. The external surfaces of the device may be enhanced to allow by additive or subtractive processes, the application of texture or osteoinductive/osteoconductive material.

The humerus implant or a joint adapter may be manufactured by using Ultra High Molecular Weight Polyethylene, or other biocompatible material suitable for use as a bearing surface in concert with a mating component of complimentary geometry.

Another aspect relates to a method for inserting a humerus implant into a humerus. The method comprises at least the steps of resecting a portion of the humerus head, reaming or drilling a larger diameter hole into the humerus head. The hole preferably has a diameter equal or slightly less than the diameter of the humerus implant with inserted locking adapter. It may further be necessary to provide a smaller diameter hole for the stem in the humerus. Alternatively, first a smaller diameter hole for the stem may be drilled or reamed into the humerus. This hole, or a stem already inserted into this holy may serve as further reference for drilling or reaming the large diameter hole. Four mounting the implant, first a stem (if used) is implanted into the humerus. It may further be cemented into the bone material. The next step is inserting a cup shaped body with its sidewall segments pressed to each other to reduce the outer diameter of the cup shaped body. The cup shaped body is oriented such, that its slot fits over the key of the stem. Then the cup shaped body is rotated to lock the cup shaped body to the stem. Now, the sidewall segments may be released, extending their locking fins towards and preferably into the bone material. After insertion of the cup shaped body into the bone, a locking adapter is inserted into the cup shaped body, thus further expanding the sidewall segments to a final position and pressing this sidewall segments towards the bone causing locking fins of the sidewall segments to penetrate into the bone. This step causes secure anchoring of the humerus implant within the bone material. The locking adapter is then fixed by a screw within the cup shaped body to the stem. In a final step, a liner, a spherical cap, or any other suitable joint adapter may be attached to the locking adapter. If only a short stem is used, it is not necessary to drill the small diameter hole into the bone. Before inserting the cup shaped body into the large diameter hole, the short stem is inserted into the cup shaped body and locked by rotation.

The present embodiments relates to a modular shoulder arthroplasty system to address preferably osteoarthritis, trauma and cuff tear arthropathy. The embodiments are not limited to such applications. It may also be used to replace any other joint. The embodiments described herein may be combined in any order.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
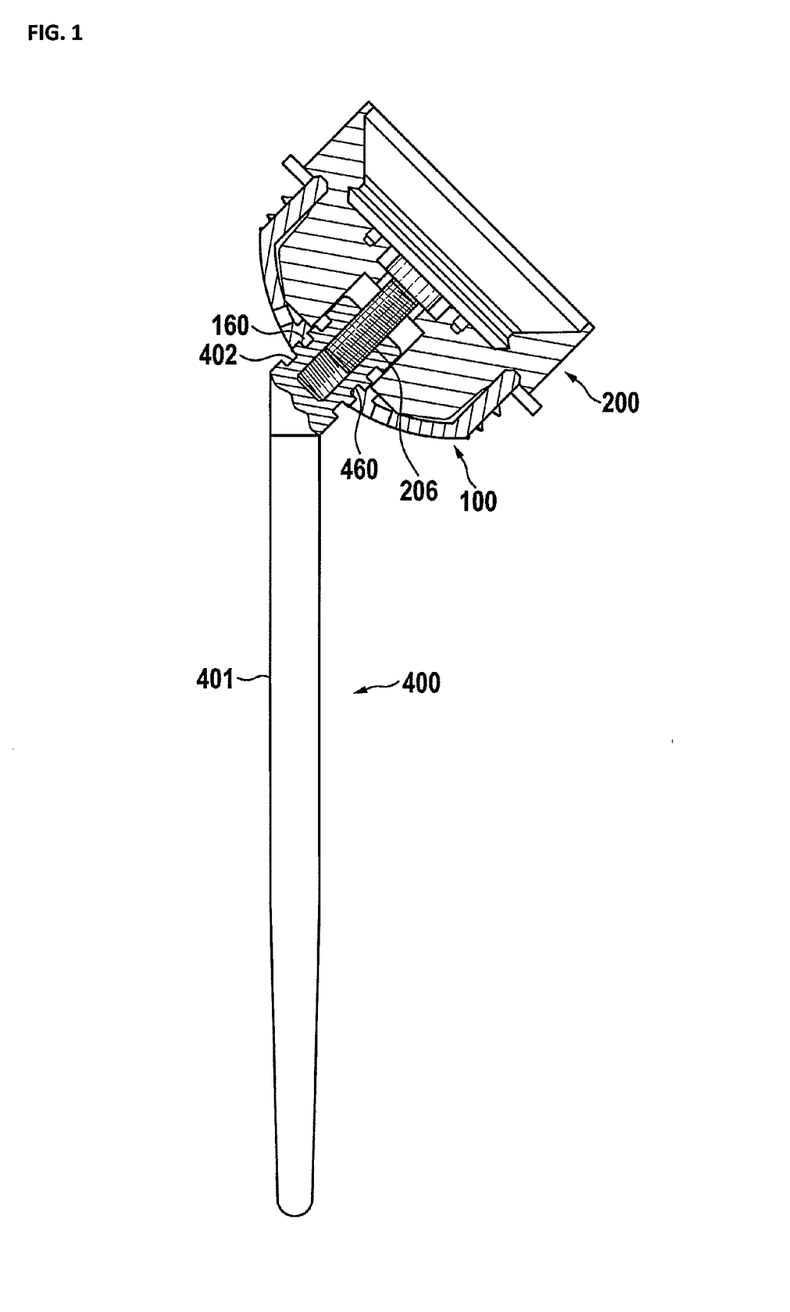
FIG. 1 shows an embodiment of a humerus implant in a sectional view.

FIG. 1 shows an embodiment of a humerus implant in a sectional view. The implant has a cup shaped body 100 with a locking adapter 200 inserted into the cup shaped body. A stem 400 having a anchoring section 401 and a locking section 402 is fixed to the cup shaped body 100. Fixing is achieved by a key 460 at the stem and a slot 160 at the cup shaped body as will be explained later. The whole assembly may be secured by a screw 206, which fits into an inner thread of the stem.

Figure 2:
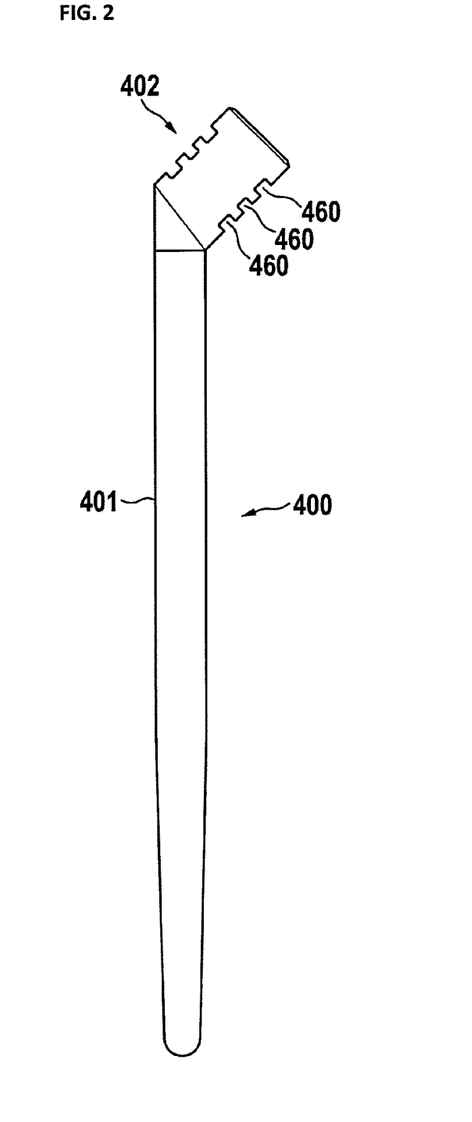
FIG. 2 shows a first embodiment of a stem.

FIG. 2 shows a first embodiments of a stem 400. The stem has an anchoring section 401, which is to be inserted into a hole of a humerus. In the stem further comprises a locking section 402, which is preferably attached under an angle to the anchoring section 401. The stem has at least one key 460. In this embodiment, three keys are shown. There may be any other number of keys. The keys allow fixing of the cup shaped body 100 to the stem 400. Different keys allow a selection of a distance of the stem 400 to the cup shaped body 100. This will be shown later in detail. The anchoring section 401 may have a length as required to provide a sufficient fixation of the implant within a humerus.

Figure 3:
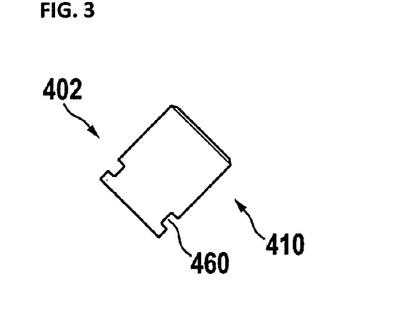
FIG. 3 shows an embodiment of a short stem.

FIG. 3 shows an embodiment of a short stem 410. Such a short stem 410 has an anchoring section of which is significantly reduced in its length. It may also have no anchoring section. In this embodiment, there is no anchoring section. There is only one key 460 provided, as an adjustment of the distance of the stem to the cup shaped body 100 is not necessary.

Figure 4:
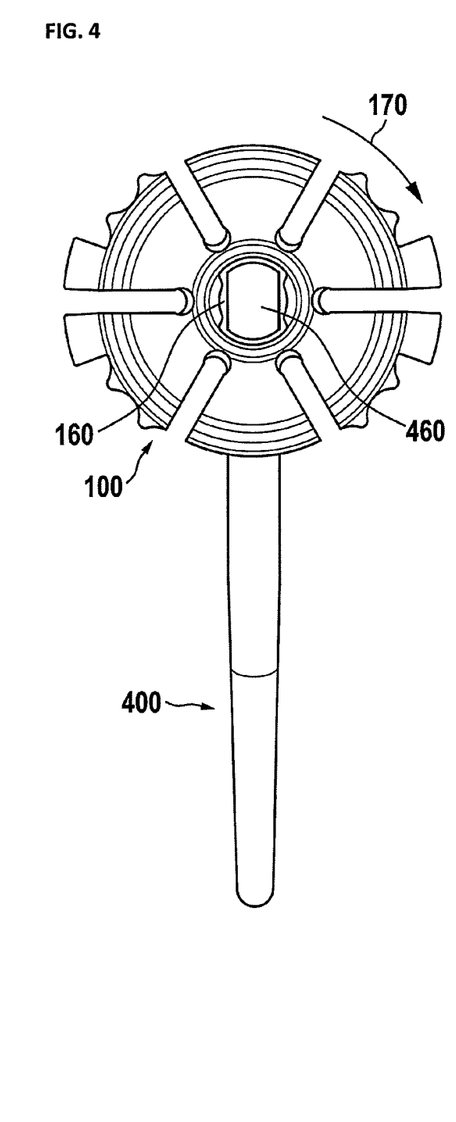
FIG. 4 shows a cup shaped body before locking to a stem.

FIG. 4 shows a cup shaped body 100 before locking to a stem 400. Here, the key 460 of the stem 400 is inserted into the slot 160 of the cup shaped body 100. For locking of this slot and key mechanism, the cup shaped body has to be rotated. Rotation is preferably done as indicated by direction arrow 170. Preferably, the angle of rotation is 90°.

Figure 5:
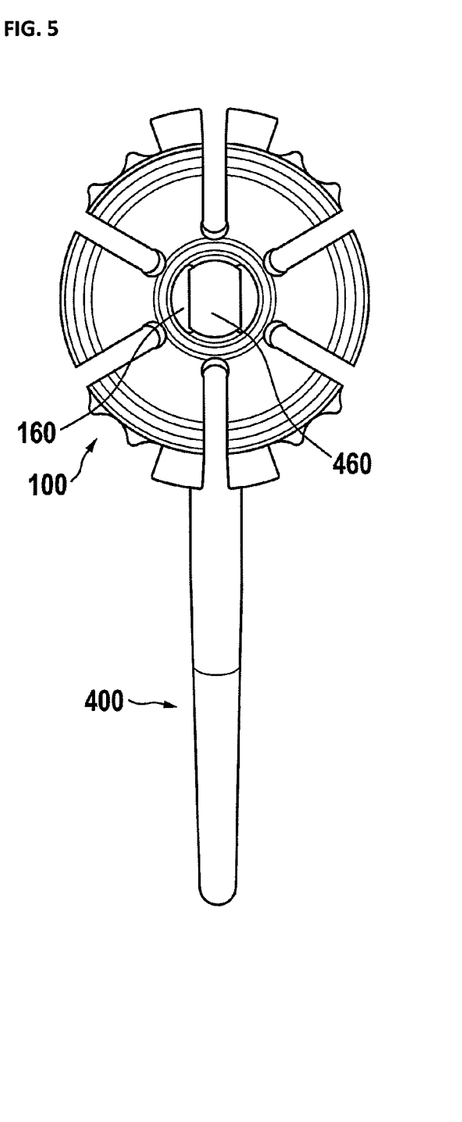
FIG. 5 shows a cup shaped body locked to a stem.

FIG. 5 shows the cup shaped body 100 locked to the stem 400. Here, the cup shaped body 100 has been rotated into the direction as indicated in the previous FIG. 4 for an angle of 90°, resulting in a locked state. Unlocking may be done by rotating the cup shaped body into the opposite direction.

Figure 6:
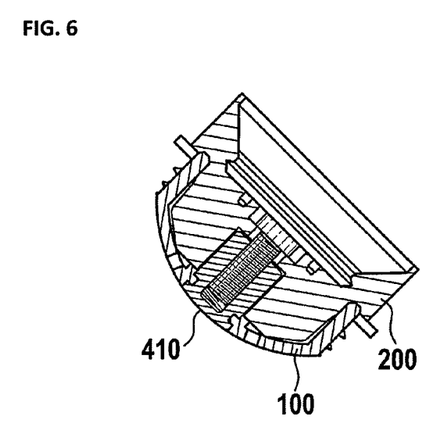
FIG. 6 shows a short stem inserted into a cup shaped body.

FIG. 6 shows a short stem 410 inserted into the cup shaped body 100. Preferably the length of the short stem is selected such, that the bottom opening in the cup shaped body is closed. Such a short stem may be used, if the retention of the cup shaped body within the bone is sufficient.

Figure 7:
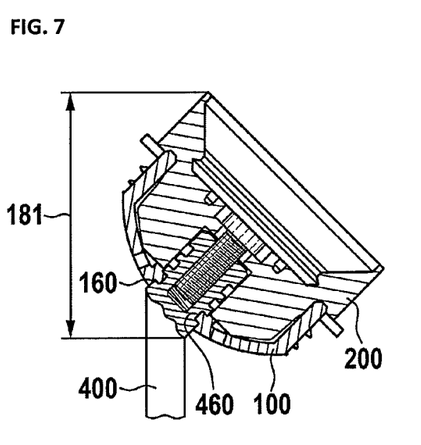
FIG. 7 shows a stem locked in a short distance.

FIG. 7 shows a stem a 400 locked to the cup shaped body in a short distance. Here, a first key 460 is used to interface with the slot 160, resulting in low total height 181.

Figure 8:
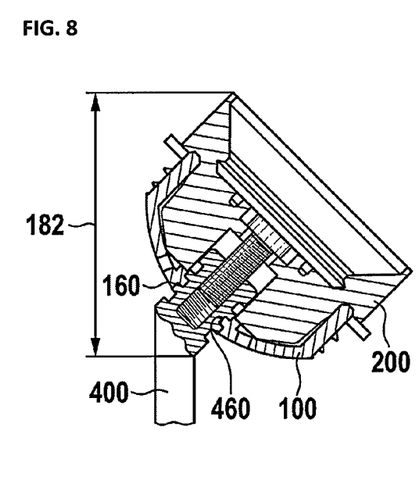
FIG. 8 shows a stem locked in a medium a distance.

FIG. 8 shows a stem a 400 locked to the cup shaped body in a medium distance. Here, a second key 460 is used to interface with the slot 160, resulting in medium total height 182.

Figure 9:
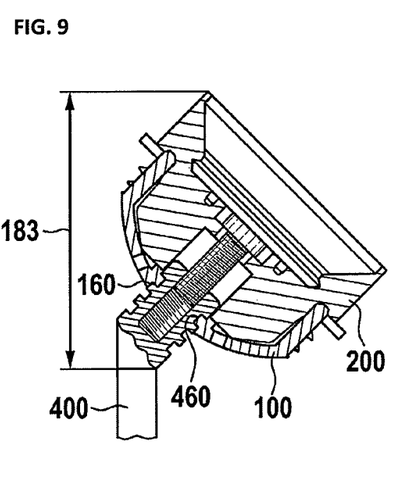
FIG. 9 shows a stem locked in a long distance.

FIG. 9 shows a stem a 400 locked to the cup shaped body in a large distance. Here, a first key 460 is used to interface with the slot 160, resulting in large total height 183. Selecting one of different keys allows for a simple selection of the total height. It is not necessary to provide different stems or different cup shaped bodies. Furthermore, selection or adaption of the height may simply be done during the implanting procedure.

Figure 10:
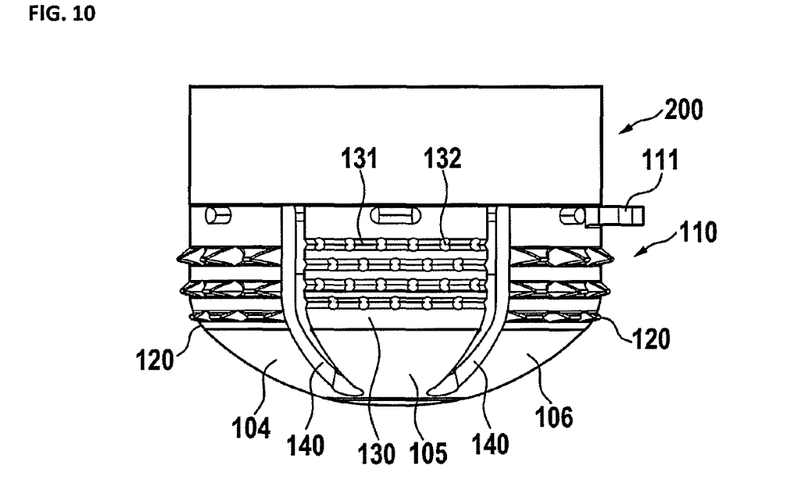
FIG. 10 shows an embodiment of a humerus implant in a sectional view.

FIG. 10 shows an embodiment of a humerus implant in a sectional view. The implant has a cup shaped body 100, which comprises of a plurality of sidewall segments. There are first sidewall segments 104, 106, 120 having locking fins 122. These locking fins immediately anchor the cup shaped body within the bone. Due to the radial anchoring in the bone material, the fins cause a comparatively high pull out force of the implant. Further cementing is no more necessary.

Second sidewall segments 130 have recesses 131 and holes 132, which allow ingrowth of the bone. The recesses increase the pull out force of the cup shaped body, while the holes block rotation. Preferably, there are gaps 140 between the sidewall segments, which allow a compression of the sidewall segments during insertion and therefore a reduction of the outer circumference of the cup shaped body. Due to be reduced circumference, the cup shaped body can easily be inserted into a hole of the bone. At least one tab 111 is provided for alignment and for increasing tilt moment of the cup shaped body as described above in detail.

On the top of the cup shaped body 100 is a locking adapter 200.

Figure 11:
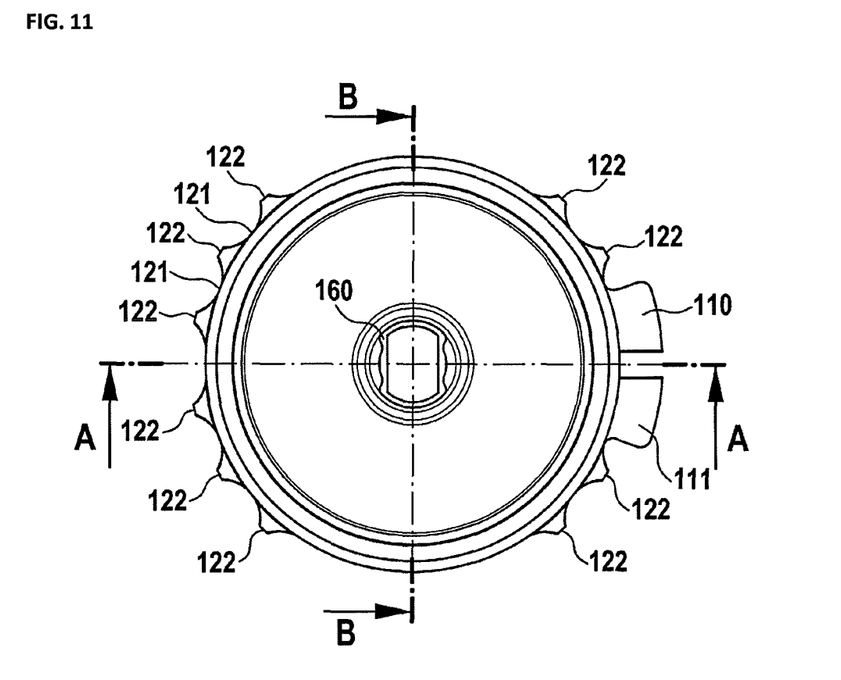
FIG. 11 shows an embodiment of a humerus implant in a top view.

FIG. 11 shows an embodiment of a humerus implant in a top view. Here, the locking fins 122 and the gaps 121 in between the fins can be seen. A screw can be inserted into hole 210 to lock the locking adapter 200 against the cup shaped body 100. Furthermore, this figure shows an arrangement symmetrically to sectional line A-A with two tabs 110, 111.

Figure 12:
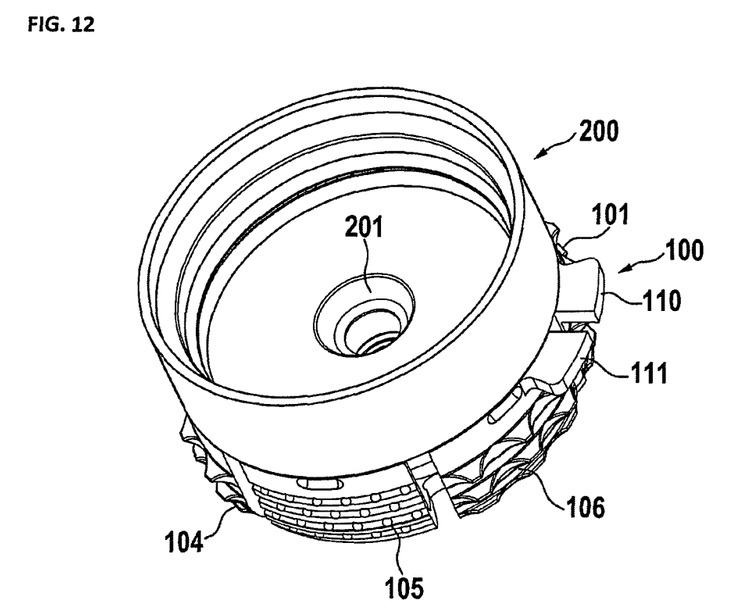
FIG. 12 shows a perspective view of the cup shaped body to the top side.

FIG. 12 shows a perspective view of the cup shaped body to the top side.

Figure 13:
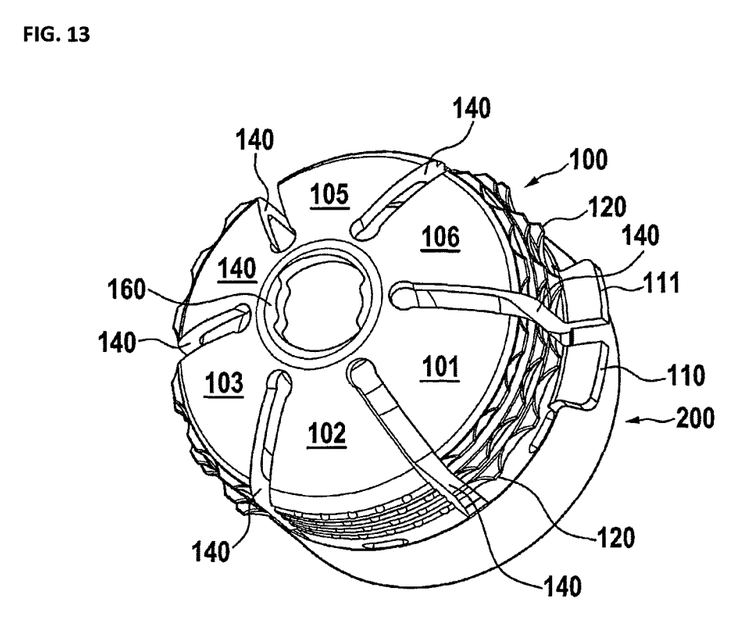
FIG. 13 shows a perspective view of the cup shaped body to the bottom side.

FIG. 13 shows a perspective view of the cup shaped body to the bottom side. Here, the sidewall segments are numbered from 101 to 106.

Figure 14:
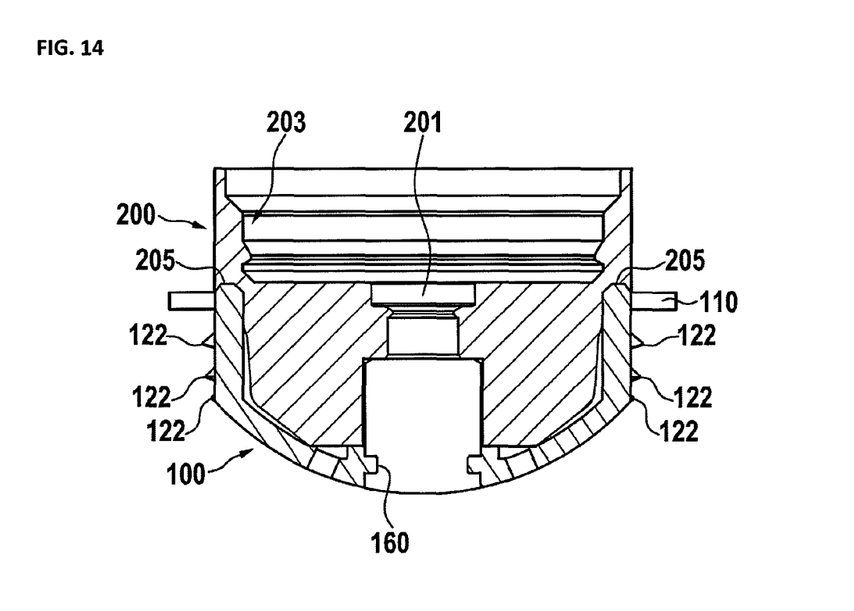
FIG. 14 shows a first sectional view.

FIG. 14 shows a first sectional view at the sectional line A-A of FIG. 2. The slot 160 is for connection to a stem. The locking adapter 200 has a hole for a screw 201. Furthermore, a conical contour is provided to simplify insertion of the locking adapter into the cup shaped body, pushing the sidewall segments to the outside until they are locked by a locking ring 205. The locking ring may also be a circular notch. The locking ring surrounds the edges of the sidewall segments to hold them firmly in their position independent of pushing or pulling forces. The locking ring may furthermore have means 203 for holding further components. Such components may be snapped into such a means.

Figure 15:
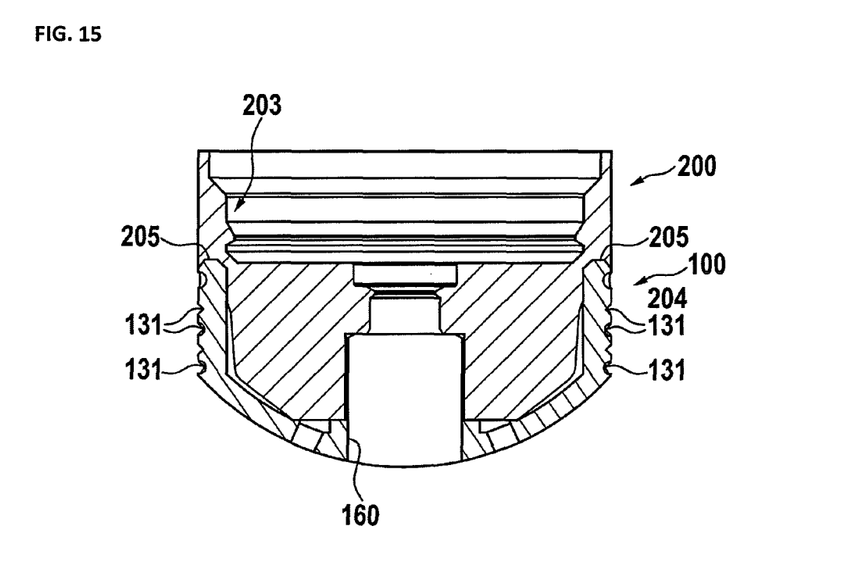
FIG. 15 shows a second sectional view.

FIG. 15 shows a second sectional view at sectional line B-B. Here, the recesses 131 instead of the locking fins of the previous figure at the outside of the sidewall segments are shown.

Figure 16:
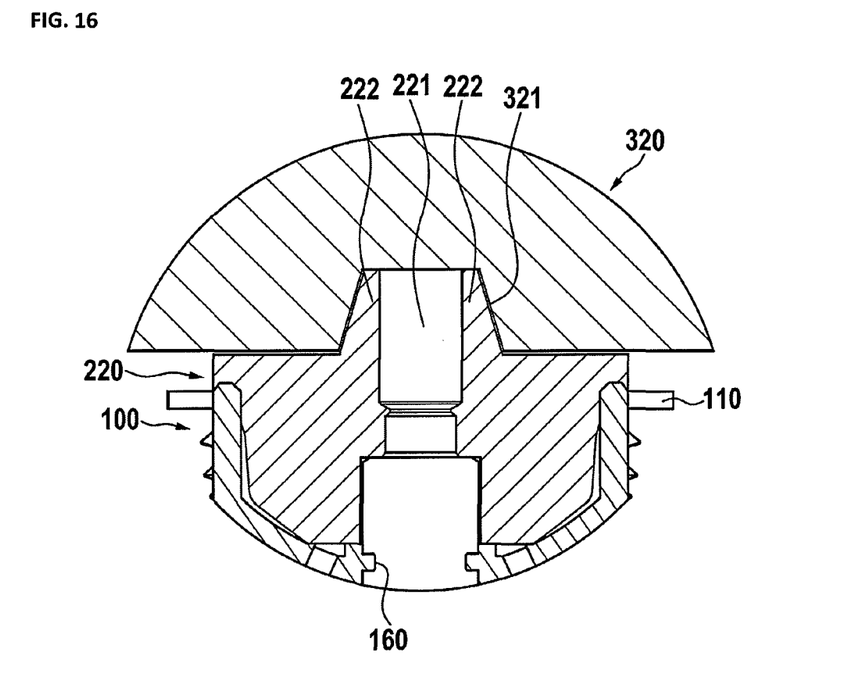
FIG. 16 shows an embodiment with a spherical cap.

FIG. 16 shows a spherical cap 320 positioned on a locking adapter 220. Here, the locking adapter has a tapered shank 222, which fits into a conical hole 321 of the spherical cap 320.

Figure 17:
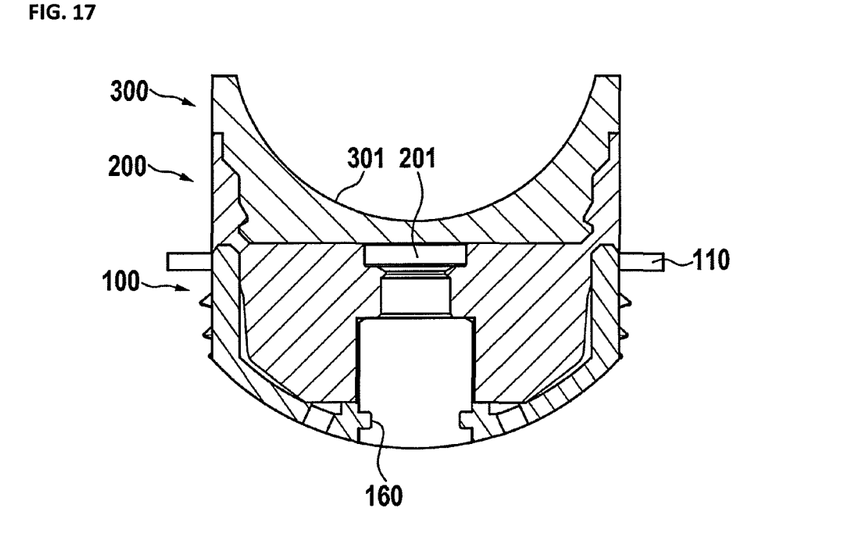
FIG. 17 shows an embodiment with a spherical liner.

FIG. 17 shows a humerus component 300 of a reverse prosthesis mounted into the locking adapter to 200 in cross sectional view. It has a preferably spherical inner surface 301.

Figure 18:
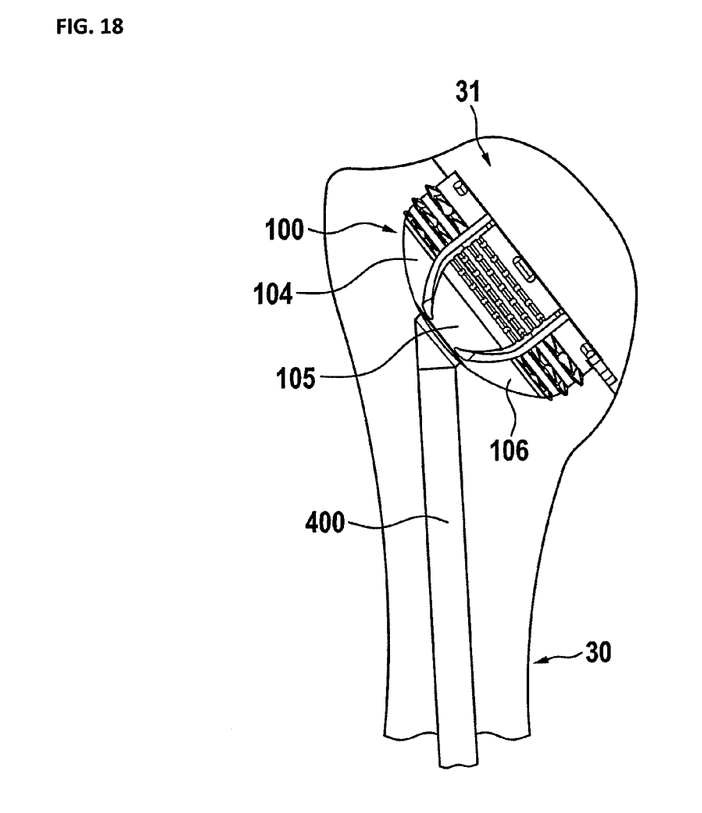
FIG. 18 shows a humerus with an inserted implant.

FIG. 18 shows a humerus 30 with an inserted implant 100 in the cancellous bone. Before insertion of the implant, the top section 31 of the humerus head has to be resected and an excavation for the body must be made. The optimum position of the implant can be selected by the position and angle under which the top section 31 of the humerus is cut away.

Figure 19:
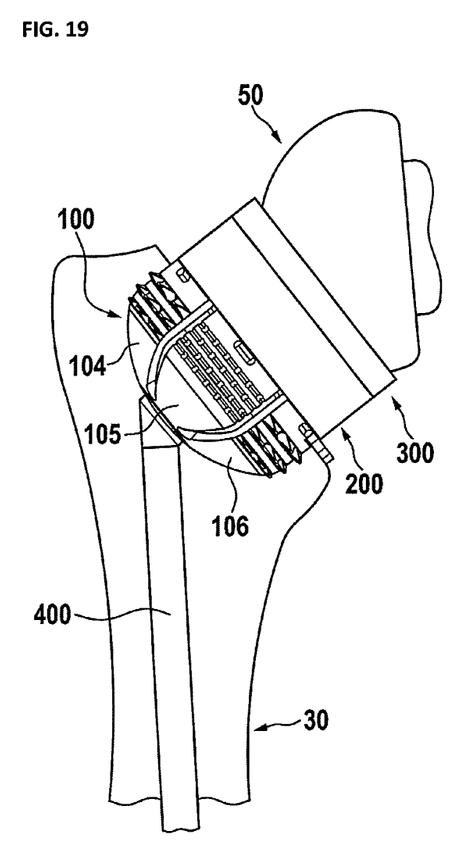
FIG. 19 shows a glenoid component at the implant body.

FIG. 19 shows a spherical liner 300 interfacing a glenoid component 50 of a reverse shoulder prosthesis (also referred as inverse shoulder prosthesis). The implant is held within a humerus 30.

Figure 20:
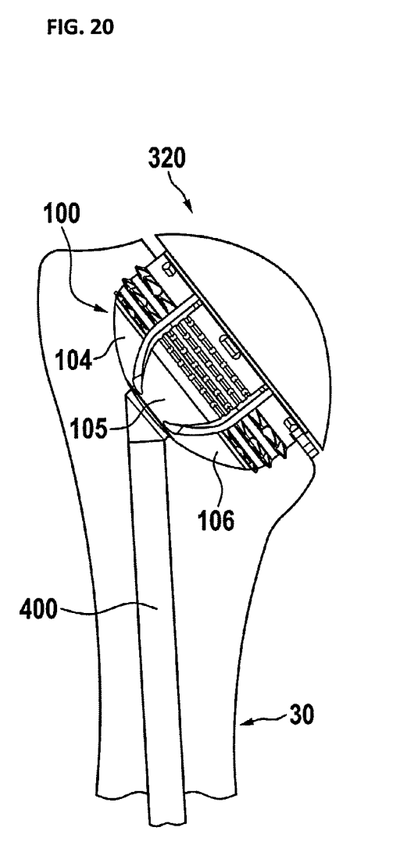
FIG. 20 shows a humerus component at the implant body.

FIG. 20 shows a humerus component 320 of an anatomical prosthesis mounted into a humerus 30.

It will be appreciated to those skilled in the art having the benefit of this disclosure that this invention is believed to provide a stemless reverse shoulder implant. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 30 humerus
31 resected portion of humerus head
32 cavity
33 hole
50 glenoid component of a reverse shoulder prosthesis
100 cup shaped body
101-106 side wall segments
110, 111 tabs
120 first sidewall segments
121 gaps
122 locking fins
130 second sidewall segments
131 recesses
132 holes
140 gaps
150 threaded hole
160 slot
170 direction of rotation
181 low total height
182 medium total height
183 large total height 200 locking adapter
201 hole for screw
203 means for holding further components
204 conical contour
205 locking ring
206 screw
210 hole for screw
220 second locking adapter
221 hole for screw
222 tapered shank
300 humerus component of inverse prosthesis
301 spherical surface
320 spherical cap
321 conical hole
400 stem
401 anchoring section
402 locking section
410 short stem
460 key

What is claimed is:

1. A humerus implant having a stem and a cup shaped body configured for contact with a humerus, the stem comprising an anchoring section and a locking section with at least one key which fits into a slot of the cup shaped body to form a key and slot connection, wherein the cup shaped body can be locked to the stem by rotation of the cup shaped body against the stem.

2. The humerus implant of claim 1, wherein the stem has a plurality of keys spaced apart in different distances to allow for locking of the stem and the cup shaped body in different distances.

3. The humerus implant of claim 1, wherein the cup shaped body has a plurality of flexible sidewall segments with gaps between neighbored sidewall segments.

4. The humerus implant of claim 3, wherein at least one of the sidewall segments has a plurality of locking fins.

5. The humerus implant of claim 3, wherein at least one of the sidewall segments has a plurality of recesses and holes.

6. The humerus implant of claim 3, wherein at least one of the sidewall segments has at least one tab extending radially from the cup shaped body.

7. The humerus implant of claim 4, wherein four first sidewall segments having a plurality of locking fins and two second sidewall segments having a plurality of recesses and holes are provided.

8. The humerus implant of claim 1, wherein the implant further has a locking adapter having means for fixing the locking adapter to the cup shaped body.

9. The humerus implant of claim 8, wherein the locking adapter has a locking ring for locking at least one sidewall segments into a final position.

10. The humerus implant of claim 9, wherein the locking ring surrounds the edges of the sidewall segments to hold them firmly in their position independent of pushing or pulling forces.

11. The humerus implant of claim 8, wherein the locking adapter has a tapered shank for attaching a further component.

12. The humerus implant of claim 8, wherein the locking adapter has means for attaching a humerus component of an inverse prosthesis or means for attaching a spherical cap.

13. The humerus implant of claim 8, wherein the locking adapter has a conical outer contour at which sidewall segments can slide during insertion of the locking adapter into the cup shaped body and are such pressed outwards towards the bone.

14. The humerus implant of claim 1, wherein the stem is a short stem.

15. A method for inserting a humerus implant into a humerus comprising the steps of:
preparing the humerus head by resecting a portion of the humerus head, reaming or drilling a hole into the humerus head, the hole having a diameter equal or slightly less than the diameter of the humerus implant with an inserted locking adapter when a locking adapter is inserted into a cup shaped body;
inserting the cup shaped body into the prepared hole with its sidewall segments pressed to each other to reduce the outer diameter of the cup shaped body;
inserting the locking adapter into the cup shaped body; and
attaching a liner, a spherical cap, or a suitable joint adapter to the locking adapter.

16. The method of claim 15, further comprising the steps of:
providing a smaller diameter hole for the stem in the humerus;
implanting a stem into the humerus;
after the cup shaped body has been inserted, rotating the cup shaped body to lock the cup shaped body to the stem; and
fixing the locking adapter to the stem by a screw.

17. A method for inserting a humerus implant having a stem and a cup shaped body into a humerus, the method comprising the steps of:
drilling or reaming a first hole in the humerus;
drilling or reaming a second hole in the humerus, the second hole having a diameter equal or slightly less than the diameter of the cup shaped body;
inserting the stem of the humerus implant into the first hole;
inserting the cup shaped body of the humerus implant into the second hole;
locking the cup shaped body to the stem;
inserting a locking adapter into the cup shaped body; and
attaching a liner, a spherical cap, or a suitable joint adapter to the locking adapter.

18. The method of claim 17 wherein the cup shaped portion of the humerus implant further comprises a plurality of compressible sidewall segments and wherein the step of inserting the cup shaped body into the second hole further comprises the step of pressing the plurality of sidewall segments to reduce the outer diameter of the cup shaped body.

19. The method of claim 17 wherein the stem of the humerus implant further comprises at least one key and the cup shaped body of the humerus implant further comprises a slot; and wherein the step of locking the cup shaped body to the stem further comprises fitting the slot over the at least one key and rotating the cup shaped body relative to the stem.

* * * * *